(12) United States Patent
Desrochers (10) Patent No.: US 9,822,406 B2
(45) Date of Patent: *Nov. 21, 2017

(54) BORRELLIA PROVOCATION PROCEDURE PROTOCOL

(71) Applicant: Dominique Desrochers, Roxbury, VT (US)

(72) Inventor: Dominique Desrochers, Roxbury, VT (US)

(73) Assignee: TITAN COLLABORATIVE KITHE, LLC, Roxbury, VT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/581,550

(22) Filed: Apr. 28, 2017

(65) Prior Publication Data
US 2017/0233793 A1     Aug. 17, 2017

Related U.S. Application Data

(63) Continuation of application No. 14/297,773, filed on Jun. 6, 2014, now Pat. No. 9,670,537.

(51) Int. Cl.
*C12Q 1/68* (2006.01)
*C12Q 1/04* (2006.01)
*A61M 37/00* (2006.01)

(52) U.S. Cl.
CPC ......... *C12Q 1/686* (2013.01); *A61M 37/0015* (2013.01); *C12Q 1/04* (2013.01); *A61M 2037/003* (2013.01); *A61M 2037/0023* (2013.01); *G01N 2800/26* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis | |
| 4,683,202 A | 7/1987 | Mullis | |
| 5,849,492 A | 12/1998 | Rogan | |
| 6,214,355 B1 | 4/2001 | Guo | |
| 6,660,274 B2 | 12/2003 | Philipp | |
| 6,794,166 B2 | 9/2004 | Godfroid | |
| 8,129,165 B2 | 3/2012 | Lundberg | |
| 8,206,930 B2 | 6/2012 | Feola | |
| 8,247,181 B2 | 8/2012 | Barbour | |
| 8,277,813 B2 | 10/2012 | Bolen | |
| 8,283,458 B2 | 10/2012 | Norris | |
| 8,303,961 B2 | 11/2012 | Lundenberger | |
| 8,318,915 B2 | 11/2012 | Anda Fernandez | |
| 8,338,566 B2 | 12/2012 | Pal | |
| 8,388,981 B2 | 3/2013 | Hoey | |
| 8,389,695 B2 | 3/2013 | Kunstelj | |
| 2006/0047242 A1 | 3/2006 | Laurent | |

FOREIGN PATENT DOCUMENTS

EP          0381410 A1     8/1990

OTHER PUBLICATIONS

A. Aberer, et al., "Molecular Mimicry and Lyme Borreliosis: A Shared Antigenic Determinant Between Borrelia burgdorferi and Human Tissue," Ann. Neuro., 26:732-737 (Dec. 1989). abstract only.

L. Bakken, S. Callister, P. Wand, R. Schell "Interlaboratory Comparison of Test Results for the detection of Lyme disease by 516 participants in the Wisconsin State Lab of Hygiene/ College of American Pathologists proficiency testing program" Journal of Clinical Microbiology 1997; 35-3: 537-543.

J.G. Donahue et al., "Reservoir Competence of White-Footed Mice for Lyme Disease Spirochetes," Am. J. Trop. Med. Hyg., 36:92-96 (Jan. 1987). abstract only.

Erol Fikrig, Tick saliva: new targeting for lyme disease vaccine : HHMI News, Nov. 19, 2009.

E. Fikrig et al., "Borrelia burgdorferi P35 and P37 Proteins, Expressed In Vivo, Elicit Protective Immunity," Immunity, 6:531-539 (May 1997).

H. Horka', Kopecky, J., et. al., Tick Saliva affects both proliferation and distribution of Borrelia burgdorferi spirochetes in mouse organs and increases transmission to ticks: International Journal of Medical Microbiology Jun. 2009; 299 (5):373-80. abstract only.

R. T. Green et al., "Immunoblot Analysis of Immunoglobulin G Response to the Lyme Disease Agent (Borrelia burgdorferi) in Experimentally and Naturally Exposed Dogs," J. Clin. Micro., 26:648-653 (Apr. 1988).

Todd Kowalski, Sujatha Tata, et. al., Antibiotic treatment duration and long-term outcomes of patients with early Lyme Disease from a Lyme disease-hyperendemic area ; Oxford Journals Clinical Infectious Diseases; 2010, 50(4): 512-520.

Peter Krause, Daniel Foley, et. al., Reinfection and relapse in early Lyme disease—.; American Journal of Tropical Medicine and Hygiene; 75(6), 2006, 1090-1094.

Clair Marchal, Frederic Schramm, et. al., Antialarmin effect of tick saliva during the transmission of Lyme disease . : Infection and Immunity 2/11; 79(2); 774-485.

(Continued)

*Primary Examiner* — Brian J Gangle
(74) *Attorney, Agent, or Firm* — Lambert & Associates; Gary E. Lambert; David J. Connaughton, Jr.

(57) ABSTRACT

The testing for the Lyme disease pathogen, (*Borrelia bergdorferi* (Bb) and all other Lyme *Borrelia*), is notoriously difficult. Bb is not by nature a blood loving bacteria, and prefers the climate of avascular tissues such as cartilage. The *Borrelia* Provocation Procedure disclosed herein proposes to uniquely lure the Lyme *Borrelia* spirochetes into the blood through a simple procedure of sub-dermal injection of benign tick saliva and co-factors. Lyme *Borrelia* can then be tested accurately after the provocation injection (BPP), utilizing any Lyme *Borrelia* detection test ideally as a specific PCR (polymerase chain reaction) test for the most accurate results as there will be abundantly available DNA present in the blood if there is an existing infection. Treatment is more effective after provocation as well, due to the same action of the Bb. The provocation protocol taught herein makes accurate, non-invasive, active direct Lyme infection testing possible, and creates a platform for an effective treatment as well.

16 Claims, 4 Drawing Sheets

(56) References Cited

OTHER PUBLICATIONS

Machackova, Martina; Oborik, Miraslav; Kopecky, Jan: Effect of Salivary gland Extract from Ixodes ricinus ticks on the Proliferation of Borrelia burgdorferi sensu stricto in vivo: Folia Parasitolgica 53: 153-158, 2006.

Picken, et. al., A two year prospective study to compare culture and polymerase chain reaction amplification for the detection and diagnosis of Lyme borreliosis : Molecular Pathology, Oct. 1997: 50(4):186-193).

A. C. Steere, 2004, J. Clin. Invest. 113, 1093-1101.

Chien-Ming Shih, Li-Lian Chao and Chia-Pan Yu "Chemotaxic migration of the lyme disease spirochete (Borrelia burgdorferi) to salivary gland of vector ticks" American Journal of Tropical Medicine and Hygiene, 66(5), 2002, pp. 516-621.

Zhang, J.-R., et al "Antigenic variation in Lyme Disease Borreliae by promiscuous recombination of VMP-like sequence cassettes", Cell, vol. 89, pp. 275-285, Apr. 1997.

J. R. Zhang et al., "Genetic Variation of the Borrelia burgdorferi Gene vlsE Involves Cassette-Specific, Segmental Gene Conversion," Infect. Immun., 66:3698-3704 (Aug. 1998).

M. Kazimirova, "Pharmacologically Active Compounds in Tick Salivary Glands", Advances in Arachnology and Developmental Biology; Institute Zool., Belgrade, Vienna, Serbia Monographs, 12, 281-296. (2008).

J.G. Valenzuela, Exploring tick saliva: from biochemistry to 'sialomes' and functional genomics—: Vector Molecular Biology Unit, NIH, Bethesda, MD. Parasitology (2004), 129, S83-S94.

Jing Wu, Yipeng Wang, et al., Two immunoregulatory peptides with antioxidants activity from tick salivary glands—: J. Biol. Chem. 2010, 285:16606-16613 originally published online Feb. 23, 2010.

J. Severinova, J. Sala't, J. Kopecky, et. al., Co-Infection of Borrelia afzelii with tick salivary gland extract influences distribution of immunocompetent cells in the skin and lymph nodes of mice; Folia Microbiologica, Sep. 2005, vol. 50 Issue 5 pp. 457-463. Abstract Only.

BORRELLIA PROVOCATION PROCEDURE PROTOCOL

FIELD OF THE INVENTION

The present invention relates to the field of human and animal diagnostic and treatment procedures for the Lyme Disease pathogens including *Borrelia burgdorferi*, et. al. More specifically this invention offers a methodology to improve the accuracy of the results of most Lyme testing technologies presently available. Treatment procedures may also be enhanced with the BPP.

BACKGROUND

Lyme Disease Background

*Borrelia burgdorferi* (Bb) is utilized herein as a generic term which encompasses several *Borrelia* species associated with, and believed to be, the causative agent of Lyme borreliosis (Lyme disease): *B. burgdorferi sensu stricto, B. garinii*, and *B. afzelii*, et. al. This disease is transmitted by the bite of various species of Ixodes ticks carrying the spirochete. The main reservoir of the infection in the United States is the white footed mouse, *Peromyscus leucopus*, and the infection can be transmitted to many mammalian species including deer, dogs, cats, and humans The first and foremost problem with Lyme disease is accurate diagnosis. There are reasons for these difficulties in diagnosis. To start, the initial bite of an infected tick may go unnoticed by the patient, and then the clinical manifestations of Lyme disease can significantly vary among diagnosed patients. Common general symptomatology such as fever, malaise, and arthritis can resemble the symptoms caused by many other conditions, further complicating an accurate and timely diagnosis.

The second reason contributing to difficult diagnosis of Lyme disease is that the primary traditional diagnostic method currently available is limited to detecting Lyme *Borrelia* antibodies which, in general, is retrospective and of little use to treating patients in acute-phase states (to be explained). Complicating the immune reaction specifically is that this infective agent sometimes invades the immunoglobulins themselves, rendering detection of an immune response utilizing antibodies impossible. Further complicating testing despite the presence of an active immune response, the disease can persist for years in patients unless it is treated early. Such persistence is postulated to be the result, at least in part, of antigenic variation in the bacterial proteins. In many cases this persistence is assumed to be from repeated exposures (infective tick bites).

The accurate diagnosis of Lyme disease in humans and animals has been compromised by the lack of definitive serology (blood testing) which should lead to rapid and accurate diagnosis, but does not. The current generally accepted diagnostic tests suffer from low sensitivity and specificity, as illustrated by a recent survey of diagnostic laboratories performance issued by the Wisconsin State Laboratory of Hygiene. A simple, sensitive and specific diagnostic methodology, and a useful serologic method of testing for the early detection of Lyme disease is presently lacking but is really needed within the art to apply effective treatments.

In addition, antibiotic therapy is highly effective, especially if administered in the early stages of infection of Lyme disease, much more than late stage infections. Early and accurate diagnosis is necessary to allow this standard therapy to work. However, serious complications can result from a missed diagnoses and inappropriate treatment. Also, there is no commercially available or useable vaccine for human Lyme disease, so the development of accurate and sensitive laboratory diagnosis is an important goal of Lyme disease research as prevention is impossible. The longer the infection is in the system, the more difficult it becomes to eliminate.

Lyme Disease is the fastest growing vector borne illness in the country according to the CDC. To date, there are no consistently reliable, non-invasive and affordable testing methods. The disease is difficult to diagnose on symptoms alone due to variations in symptom patterns.

Treatment offered beyond the 7th day from the initial infection period shows more relapse responses and bacterial resistance to treatment. As time goes by, treatability becomes progressively more difficult. These spirochetes adapt to chemical (antibiotic) assault with adaptive genetic coding shifts, and maintains the information for future generations. The spirochetes are even known to have migrated to the central nervous system before the erythema migrans rash erupts.

Spirochetes will also rapidly congregate in tendons and joints, making it more and more difficult to access the pathogen for testing as it moves deeper into tissues over time. This pattern also makes it exceptionally difficult to eradicate when the *Borrelia* moves into these non-vascular synovial fluids and nervous tissues utilizing the treatment of blood borne antibiotic treatments.

Difficulties with proper detection remain an issue with the testing protocols presently recommended by the CDC, which has a serum only requirement, and utilizes the Western Blot and ELISA as their base standard.

The Lyme spirochete's natural mode of operation is to undergo alterations in their physical form (DNA) within the tick before transmission. The spirochetes change their genetic structure to adapt to the present carrier species as well. As it lives within a carrier, it will modulate its form utilizing the extra DNA fragments it carries to avoid immune detection. This is beyond epigenetic adaptability. These factors make it very difficult to accurately test antibodies and antigens with these variable triggers.

If the infected tick implantation is successful, it takes the tick born spirochetes 24 hours to identify this host, alter its DNA and transfer to the host mammal. After transfer, they will peak in numbers 60 days into the infection and then drop by a factor of 1000 making them almost impossible to detect there after within the blood. This is a public health issue as many people are not even aware of the tick bite and the time line associated.

Established research has shown the *Borrelia* organisms are present in very small numbers in the body, and are often sequestered in hard to reach places that require biopsy. Antibodies are sometimes so low or non-existent in infected individuals that they do not show positive in blood tests. Antibodies create other confusion in accurate diagnosis because they can continue to be produced, even if the infection has been eradicated.

A more difficult and impractical solution for the issue of Lyme disease will be the formulation of a vaccine to prevent this infection. The DNA structure varies and adapts to the species quickly, making it nearly impossible to create an effective human vaccine, without creating a variant of the disease or autoimmunity, which was a problem with previous attempts. Needle transmission of the isolated spirochetes creates a very different serum antibody response than a natural tick bite transmission. There is also an extremely small immune response to the spirochete alone.

Rapid treatment is the most viable and effective defense at this time. Several antibiotics work very effectively when treatment is prompt, relative to the infection onset. If there are no active Lyme Borrelia spirochetes, Lyme treatment protocols are not indicated, and alternative diagnosis procedures are indicated.

If the white blood cells themselves become infected with the spirochete, an immune response does not occur at all. Since there is tick saliva present with transmission, leukocyte (immune response) activity becomes suppressed by the saliva itself. As a result the ELISA test is quite unreliable as it is only testing certain antibodies.

The antibody schedule that typically will occur is as follows:
  Week 2-4—½ of people infected will produce antibodies, only to disappear by week 8
  IgM antibodies rise during the third week, peak at week 4-6 and disappear at week 8
  IgG antibodies can persist for years or decades, creating false positives even if there is no active infection.

A second bite seems to change this classic timing patterns. The peak in this case is around day 6 (according to species and organ load measured). Secondary tick bites seem to convey a certain amount of immunity and do not always stimulate a flair of immune responses or infection symptoms. Choosing and using the right antibody mediated testing procedure at the right time seems impractical.

These are significant problems impeding accurate detection of Lyme disease infection, and therefore proper treatment.

Only extremely healthy people with very healthy immune systems can produce antibodies to the tick saliva to inhibit future tick implantation, or produce tick rejection. The more immune compromised an individual is, including simple generalized stress response, the more likely it is that infection will take place, the antibiotics can fail, and there will be a relapse into so called, long-term Lyme syndromes.

The Western Blot has its own issues, as much of the test depends on antibody reactive band activity from any flagella from any form of spirochete and is not Lyme specific so it can also include all Treponema spirochetes, including those that cause syphilis, yaws and periodontal infections.

Unfortunately the Western Blot and the ELISA tests are presently the gold standard of Lyme testing in the field, primarily because they utilize blood as the testing source. The commercial labs and hospitals and so forth tend to use one antigen test, when there are many, and they are notoriously under-diagnosing Lyme disease due to this lack of consistency. False negative testing can lead the patient being up to 20 years on the wrong treatment pathway medically.

Related Lyme Borrelia Behavior Background

The scientifically established and determined normal behavior of the Lyme Borrelia spirochete is the key focus of this procedure. When there is a behavior that has a stimuli and response action, it becomes artificially manipulable. Manipulating the natural behavior of the Lyme spirochete makes it more precisely testable.

The Lyme Borrelia organism is one of the most adaptable and changeable organisms on the planet. This spirochete can rapidly change its genetic structure to adapt and respond to any environmental pressure. For example, when the spirochete is being starved by its tick host it has the extreme morphic ability to change into an encysted form within one minute of being genetically expressed in order to await a more favorable environment or host (up to ten months). They can do this as a result of possessing and utilizing the largest number of optional genetic units of replication of any bacteria known.

Though all Borrelia groups are classified as spirochete bacteria, they behave as exceptionally intelligent protozoa. Having predictable behaviors makes it possible to manipulate these spirochetes. The traditional approaches to manipulating or controlling bacteria with antibiotics or vaccines does not work as well as hoped for with these organisms as they also possess a unique flexibility in that they can rearrange their genetic structure appropriately through chemotaxis to avoid detection and create resistance. (Chemotaxis=the detection of minute changes of the chemistry of their environment). These spirochetes also have a great ability for multi-drug efflux as they become exposed to new treatment medications. (Efflux=organism develops the ability to have the killing drugs flow out of them before they can do harm). With this disease, it is uniquely important to manipulate and control these reactions to rapidly and effectively detect and treat the infection when the pathogen is vulnerable.

All Borrelia spirochetes also utilize chemotaxis for monitoring and adapting to the changing worlds it can live in. It extends survival. For example, chemotaxis is used to detect when the spirochete's host (tick) is feeding, as well as identification of what species it is feeding upon. There are 24 extra segments of DNA available for the spirochete's use at any time to adapt to a new host's environment. This is dependent upon the detection and identity of the DNA of the tick's new and future host (mammal), as detected by the spirochete through the host blood upon which the tick is feeding.

The Lyme Borrelia then will sort out which strands will be utilized, and the organisms communicate with each other to modulate the correct variations of DNA strands to ensure the greatest survival in the new host, splicing in the new variables. These DNA strands contain information on how to make changes to the Lyme Borrelia's own physiology to evade that mammal host's immune system. This Borrelia strain will hold that memory for future generations to use as well. When that configuration is internally calculated, the spirochetes triple to quadruple their population in preparation for transfer to the mammal host. As prior arts have established, 154 genes in all are altered in this process (75 are up-regulated and 79 are down-regulated). Thirty-seven changes occur in the outer protein membrane alone, as discovered thus far. These are extremely difficult parameters when considering vaccines, tests, and treatments. The variations are almost limitless.

At this stage the spirochetes are within the saliva of the tick vector. The Lyme Borrelia moves into the mammalian host through this exchange of blood and saliva. It genetically alters itself once again as a group to penetrate the epithelial tissues, creating more collagenolytic, fibrinolytic and proteolytic products beyond the activity of just the tick saliva to facilitate this process. Once cloaked in its invasive identity, the spirochetes move slowly through the blood of the mammal host, seeking collagenous and dense tissues. The Bb as all Borrelia share the same lack of preference for blood and a strong affinity for dense collagenous tissues. They move even faster in collagen than in blood. Some of the densest tissues are across the blood brain barrier. This is why within days of infection Lyme can be detected in the central nervous system of the host and in the aqueous humor of the eyes. The organism can be detected soon after that, in and around joints in the synovial fluid, evading immune and pharmaceutical attack, because it has already transferred out from the blood-rich tissues.

The solution starts with the tick's participation. When any growth stage of a tick vector starts to feed, it alternates between ingesting blood and secreting saliva into the wound it produces. The saliva is composed of a complex blend of powerful, pharmacologically active compounds, designed to bypass the host immune system and awareness as well as to prevent clotting. As soon as the new tick begins releasing this unique blend of chemicals and bio-factors into the blood stream of the mammal host with its saliva, the Lyme *Borrelia* in the tick begin transforming in preparation for transfer.

The genetic expression of adaptability continues once the spirochete is in the mammal's human's system. The Lyme *Borrelia* will adjust and adapt continuously to the individual person's body and immune system to better survive over time. The offspring are extremely well adapted to live in that particular person or organism as generations reproduce. Lyme *Borrelia* reproduce themselves every 8-12 hours (unlike most bacteria which is every 20 minutes). The replication period for this bacterial invasion is much slower, but more effective than other bacteria in consideration of these genetic modifications.

Lyme *Borrelia* will also create a defensive reaction on the genetic scale, releasing a "bleb" of DNA material to distract the host's immunoglobulin reactive system long enough for the Bb to transmute their own DNA to express differently. The sensitivity of the Lyme *Borrelia* spirochete allows them to detect the tiniest alterations in the surrounding environment and respond almost immediately through chemotaxic detection and genetic alteration. The same chemotaxic process is at work when the spirochete living in the host mammal detects another tick implantation.

This is the final and most relevant biological and behavioral manifestation of the spirochete. Once tick saliva factors are sensed by existing spirochetes within a tick's mammalian host, the spirochetes immediately enter the blood stream from wherever they are living and flow toward the site of the new tick attachment, attracted by the rising level of the tick saliva biofactors, as demonstrated through the pertinent research studies of Chien-Ming Shih, et al. This is the key chemically triggered behavior required to facilitate spirochete transfer to this new tick to be carried successfully to, yet a new host. Now this new tick becomes infected with Lyme *Borrelia* spirochetes, and the tick and spirochete duo are ready to reproduce, search for, and infect another mammal.

These events are intimately and uniquely connected to and controlled by the make-up of tick saliva factors. The full range of the effects of the hundreds of chemicals in the saliva are still being determined, as it is extremely complex. The identification of the new mammal host, the adaptation to enter the host and survive the host's immune system, the accelerated proliferation of the spirochetes, the detection of a new tick on the host, and the transfer into the new tick are all connected and mediated by tick saliva factors. The pertinent prior studies firmly demonstrated this phenomenon with mice.

The biggest problem for discovering a methodology of manipulation of this organism is that all *Borrelia* spirochetes are not stable in vitro (test tube), and only relatively so in vivo (living organisms). In other words, it has to be manipulated within the host in order to produce consistent results.

The collection of these established scientific observations and researches have created a knowledge base. Each avenue of research is an individual phenomenon, each as an entity unto itself. Coordinating and selective association of these data, and controlled application methodologies create a directed process for improving infection detection and treatment of Lyme disease.

The observed natural phenomena of the tick/spirochete relationships of actions and reactions create a platform of controllable variables for manipulation. Manipulation of a natural response to create an action within an unusual and predictable timeframe is essential to detect these pathogens.

Lyme spirochetes contain the largest number of genetic units of reproduction (DNA replications) of any bacteria known. They have no close relatives, genetically. The closest is the *Treponema* spirochete (syphilis) at 40% similar (which also can trigger a false positive with a Western Blot test). This makes active live Lyme disease very specific to detect with larger quantities of spirochetes in the blood, especially utilizing PCR diagnostic tests, if the spirochetes can be drawn directly into the blood stream.

Some of the difficulties in detecting the Lyme pathogen include the Lyme spirochete undergoing alterations in its physical form and encysting, waiting for a better time to re-activate (i.e. detection of a fresh new host). They can also rapidly change their chromosomal structure in response to environmental pressures. These organisms also change their genetic structure to adapt to the present host and their immune system. The spirochete populating adapts with differentiation from information from past infection hosts, creates a dormant or hidden infection, and the present infection can be virtually impossible to directly detect by testing blood, due to low incidence in that tissue.

Therefore, what is required is a way to manipulate Lyme *Borrelia* and co-infective pathogens in a controlled fashion to draw them into the blood stream, so that they are easily detected with extreme accuracy in an extraordinarily non-invasive and safe fashion. Successful manipulation of the Lyme *Borrelia* into the blood stream will allow for testing utilizing the PCR tests presently available, only if the serum is drawn within the time frame of diffusion toward the site of the tick saliva entry region, as demonstrated by Chen-Ming Shih, et al. in their researches demonstrating peak diffusion beginning at 24 hours and cresting at 48 hours.

In addition, drawing the Lyme *Borrelia* into the blood stream increases the blood concentration of the spirochetes and the lower concentrations within dense tissues connected with the use of this procedure. It is suggested that the spirochetes may also be more effectively eradicated in this phase as well. The infective agent's vulnerability at this time is the highest and will be more susceptible to traditional treatments.

BRIEF DESCRIPTION OF THE FIGURES

FIG. 1 provides an elevation view of an embodiment of a suggested injection device.

FIG. 2 provides an elevation view of another embodiment of an injection tine device.

FIG. 3 provides a partial cut-away view of an embodiment of an injection tine device.

FIG. 4 provides another partial cutaway view of an embodiment of the injection tine device.

FIG. 5 provides a view of an embodiment of administration of the *Borrelia* provocation procedure on anterior lower arm.

FIG. 6 provides a view of an embodiment of administration of the *Borrelia* provocation procedure.

FIG. 7 provides a flow chart of an embodiment of a method of testing for Lyme *Borrelia*.

SUMMARY

The testing for the Lyme disease pathogen, (*Borrelia bergdorferi* (Bb) and all Lyme *Borrelia*), is notoriously difficult. The traditional methodologies of testing are extremely outdated given the established known behavior of the Lyme spirochete, specifically the behavior of developing mutations within itself in order to detect the identity of the carrier and avoid the immune system of that particular species by intentional mutational shift. Therefore it is counterintuitive to test immune reaction activity of the infected individual. To test for the bacteria itself should be the goal, but there has to be enough testable DNA material in the blood. Bb is not by nature a blood loving bacteria, and prefers the climate of avascular tissues such as cartilage. The *Borrelia* Provocation Procedure (BPP) protocol proposes to uniquely apply several previously known arts in combination with any device of application. The BPP lures the spirochetes into the blood through a simple procedure of dermal injection of benign, uninfected tick saliva and co-factors. Lyme *Borrelia* can then be tested most accurately 24-48 hours after the BPP, primarily utilizing, for example, any Lyme *Borrelia* specific PCR (polymerase chain reaction) test for the most accurate results, as there will be abundantly available DNA present in the blood if there is an existing infection. Treatment is more effective at this particular time as well.

The *Borrelia* Provocation Procedure (BPP) is a process designed to accentuate and improve Lyme disease testing, and create treatment effectiveness by luring Lyme *Borrelia* spirochetes out of dense avascular tissues and amplifying concentrations in the blood through utilizing bio-identical tick saliva factors and co-factors injected into the dermis. This is accomplished with a prepared, dose specific device, specifically for this purpose. The BPP is followed up using any established and appropriate testing modality for the pathogen itself, not the immune response. Utilizing the *Borrelia* Provocation Procedure (BPP) protocol will define infections accurately and definitively, making treatment timely and effective. Other co-infections may also become more detectable with the BPP and therefore become treated in a more timely fashion as well. In addition, this protocol will likely lead to more effective treatment procedures through creating a timing specific antibiotic bioavailability of the spirochete pathogen. Through the creative and unique combination and utilization of previously researched diverse prior arts and sciences, the use of any appropriate application device, and the proper timing as set in these parameters, a new methodology of Lyme disease detection accuracy is created. Lyme disease will become more controlled over time within the endemic environment of increasing infection rates, providing more effective and timely intervention. The BPP protocol makes accurate, non-invasive, active direct Lyme infection testing possible, and creates a platform for an effective treatment plan as well.

The *Borrelia* Provocation Procedure protocol is based upon the intentional and artificial manipulation of a naturally occurring phenomenon to facilitate accurate Lyme Disease testing. It is accomplished through the application of any form of intradermal injection device, controlling the dose and depth and dispersion rate of tick saliva gland factors as an activating agent into the human dermis to purposefully stimulate the mobilization any Lyme *Borrelia* species directly into the blood, providing a testable concentration platform of pathogens. The full procedure involves the process of injecting the tick saliva factors into the skin of the patient, waiting 24-48 hours for mobilization of the spirochetes into the blood, and providing appropriate testing, primarily utilizing any available species specific PCR (Polymerase Chain Reaction) detection test for any Lyme spirochete factor. The use of this procedure creates the most viable testing platform producing greater sensitivity, specificity and accuracy of Lyme testing.

Problem Summary:
  a. *Borrelia* is difficult to test in human blood. Bb lives in the central nervous system, joints, and connective tissue. Lyme *Borrelia* spirochetes do not prefer to live in the blood stream, at least not in significant amounts, so these pathogens can easily be missed when testing only blood.
  b. Antibodies are not always produced by the carrier. Often the white blood cells are corrupted by the spirochete, and will therefore not create antibodies. Traditional Lyme disease screening depends on specific immune responses only.
  c. Testing tissues other than blood is more invasive to the patient, creating medical complications and unnecessary expense.
  d. False negatives and positives contribute to the problem of inappropriate or delayed treatment. 41-55% of tests result in false negatives. For example, only 10% of those with the defining erythema migrans rash will sero—test positive, though the rash itself confirms the diagnosis.

Natural Metabolism of *Borrelia bergdorferi* Summary:

Once already established in the human body, the Lyme *Borrelia* spirochete will detect the presence of another host (tick) as being available to facilitate transfer through tick saliva triggers in the blood.
  e. The saliva of the tick acts on the host body to suppress pain response, increase blood flow to the area, modulates the host's immune system, and prevents clotting. As this is going on, the Bb in the cartilaginous tissues of the host mammal detect the presence of tick saliva which signals the Bb to flow into the blood (not its preferred environment) in order to get to the new host tick. Thus the spirochete pathogen is drawn to the new tick host through the blood to enable the transfer.
  f. Spirochetes are released into the blood from dense avascular tissue, its natural habitat, in order to become ingested along with the human/mammal blood into the new tick host system to await transfer to new carrier.
  g. There are more than 400 proteins in the tick saliva of which only some functions are known. These combined factors appear to make this transfer more probable. This also makes utilization of a single saliva protein factor to stimulate migration very unlikely, so all factors of tick saliva should be theoretically used.

Theory:

If, for example, "tick saliva" is artificially introduced into the system, for a short period of time one of three things will happen:

1) The actual spirochete moves into the blood and is 100% detectable
  A. Perform a *Borrelia* specific PCR type test using a digital PCR machine detection system, already established and in standard use
  B. Testing and accurate diagnosis is complete within 24-48 hours 2) Antibodies may be triggered if the body can recognize the mobile Bb organism (one week to ten days)
   A. Perform an ELISA test
   B. Secondarily, perform a Western Blot test
3) There is no spirochete Bb or other related pathogen present, and therefore any testing for actual pathogen (PCR) will be negative.

Process in Brief:

Utilization of some form of injection methodology to introduce tick salivary gland extracts (SGE) into the skin of the patient. These methodologies are utilized to mimic the introduction of a small amount of tick saliva and possibly keratin into the skin, and to the capillary blood to most accurately mimic the natural tick bite. The Bb pathogen will be on the "blood radar" within 24-48 hours after this provocation.

Solution #1:

A patient being testable very soon after a bite will speed the appropriate use of antibiotics, which are 70-90% effective if Lyme is treated early. If not treated, the treatment effectiveness rapidly drops to 60% with a 35% relapse rate. The longer the Lyme *Borrelia* remains untreated, the more difficult it can be to eradicate, leading to long term antibiotic use.

Solution #2:

Knowing that there is an active Lyme spirochete in the system is critical to dictating appropriate treatment, as compared to the situation of antibodies being detected but there is no longer a pathogen present. Likewise, not knowing a cloaked pathogen is there and missing treatment can be avoided as well.

DETAILED DESCRIPTION

The detailed description set forth below in connection with the appended drawings is intended as a description of presently preferred embodiments of the invention and does not represent the only forms in which the present invention may be constructed and/or utilized. The description sets forth the functions and the sequence of steps for constructing and operating the invention in connection with the illustrated embodiments.

1. As used herein the term Bb, *Borrelia bergdorferi*, all refer to the entire class of infective agents inclusive and called Lyme *Borrelia* interchangeably. This includes, but is not limited to, *Borrelia burgdorferi, Borrelia garinii, Borrelia afzelii, Borrelia bissettii, Borrelia hermsii, Borrelia japonica, Borrelia lonestari, Borrelia lusitani, Borrelia spielmani, Borrelia tankii, Borrelia turdae, Borrelia turicatae, Borrielia mayonii*, and *Borrelia valaisiana* strains.

2. As used herein the term BPP refers to the *Borrelia* Provocation Procedure, in any method utilized.

3. As used herein the term SGE refers to the active ingredients of tick salivary gland extracts, whether natural or artificially created, or modified.

4. As used herein the term PCR refers to the long established Polymerase Chain Reaction procedures referring to the pertinent prior arts of detection of the chemical chains of *Borrelia*.

*Borrelia* Provocation Procedure Contents:

1) Tick saliva—(standard field procedure of SGE isolation):
   a. A selection of Lyme (−) and pathogen (−) ticks are sourced. (For example, the University of Neuchatel maintains a tick colony for such situations.) The standard SGE (salivary gland extraction) procedure is an example of the process of natural source extraction of product.
2) Injection: A bolus containing a small amount of tick saliva factors (45 micro grams max) is injected into the dermis with a single dermal needle or by piercing the dermis with injecting tines. In one embodiment, the most ideal injection site will be at the location of the front of the same lower arm, which will be phlebotomized later. The injection tines device is a significant and unique modification of the original, but no longer utilized, tuberculin tine type test for tuberculosis, and is shown in the figures herein.
   a. Most protein bands should be used to mimic the actual tick bite.
      i. Immunoregulatory peptides include—hyalomin-A and hyalomin-B (identified from the salivary gland of the hard tick *Hyalomma asiaticum asiaticum*): Anti-haemostatic factors: Anti-Inflammatory factors: Anti-Serotonin factors (binding histamine and serotonin): and bradykinin modulators.
      ii. Include the pharmacologically active components of the tick salivary proteins (Valenzuela). Salp15 protein is not a required factor, as it only mediates the spirochete cloaking.
   b. Ramification variant: An injection tine device should contain needle injection depths chosen specifically to imitate the depth of the hypostome of the feeding tick in different phases; specifically—0.14 mm, 1 mm, 1.25 mm, and 2.75 mm. A 3.25 mm should be included for the larger variants of ticks worldwide, particularly associated with Asian species. This variation of staggered tine depths will mimic the slow introduction of saliva into the host via the hypostome.
   c. Ramification variant: A keratin matrix would slow the introduction of these factors into the blood, mimicking the slow introduction by the ticks themselves and is of greater importance if single needle injection method is used. Ticks produce a keratin substance in association with their bites, so will not interfere with the SGE attractant qualities.
3) Waiting Period: The time of injection to the time of serum withdrawal is ideally within a 24-48 hour period. The ideal period for highest spirochete migration seems to be 48 hours, in vitro. (This information is to be included with any BPP device, as detailed laboratory site instructions and also a patient handout). There is a decreasing concentration over the next 8 days, making the test progressively less sensitive past 48 hours, but is still somewhat effective from day 2-5. The blood draw should ideally be in the same extremity as the BPP for the highest concentrations. In one embodiment, the blood draw may take place within approximately six inches from the BPP injection site. The use of a standard blood draw maintains the CDC accepted guidelines, reduces the cost, reduces adverse events, and increases the availability of accurate testing.
4) Testing: The standard PCR (polymerase chain reaction) test can be most effectively used in this case to detect Lyme *Borrelia* DNA. Any *Borrelia* specific PCR test will perform with more accuracy within this methodology than previously demonstrated with serum PCR testing in past attempts due to the low pathogen concentrations in the blood. With the PCR test, the process is to detect the *Borrelia* DNA directly, where there is no dependence on the unpredictable immune responses of the patient, as with the ELISA test. However, it should be understood that other tests capable of detecting a presence of Lyme *Borrelia* in blood may be used without straying from the scope of this invention.
  a. Ramification variation—Testing—: The FISH (fluorescent In-Situ Hybridization) test for *Babesia* (a co-infection) can be utilized if desired at that time. This is a standardized test based on direct microscopy for RNA of the *Babesia*. Appropriate treatment can be applied as a result.
  b. Ramification variation—Testing—: Using the BPP to stimulate other co-infections and tick born infective agents to mobilize into the blood. Any other specific diagnostic procedure could be performed at this time, relative to the antibody response times previously defined.
  c. Ramification variation: A unique variation of use is a non-shellfish keratin based carrier agent. This would significantly slow the dispersion rate of the protein factors if injected with the saliva bolus. If the dispersion of the saliva is too rapid, it is possible it may not trigger the spirochete's natural attraction pattern. Keratin additions would slow the rate of saliva dispersion without significant side effects. Any useable keratinocyte cell culture procedure may be used.

5) Treatment Ramification: Use of the BPP protocol mobilizes the pathogen out of avascular, dense tissues and into the circulatory system. The peak appropriate start of antibiotic treatment should occur at 24-36 hours, post *Borrelia* Provocation Procedure. At this point, through the BPP utilization, the pathogen population is temporarily available and vulnerable due to migration from dense tissues into the blood. Initiating treatment by manipulating the infective agents into the blood establishes a very accessible treatment location for antibiotic therapy. In this paradigm, the standard antibiotic treatments effectiveness ratings will improve. This is a unique pre-treatment modality possibility, and no references have been located on this possible avenue to provide treatment upon artificial manipulation.

EMBODIMENTS OF INVENTION

A. Embodiments may be used to enhance the detection of Lyme disease in humans at any stage of the infection.
B. Embodiments may be used to enhance the detection of Lyme disease in animals. This utilizes the same processes as described for the human model.
C. Embodiments may be used in the treatment of Lyme disease and its associated co-infections. Through the use of the BPP to move more of the spirochete pathogen into the blood and surface tissues, as it makes the pathogen more bio-available for easy eradication through antibiotic use.
D. The present invention is described by reference to an example. The use of this and other examples anywhere in the specification is illustrative only, and in no way limits the scope and meaning of the invention or of any exemplified form. Likewise, the invention is not limited to any particular preferred embodiments described herein. Indeed, modifications and variations of the invention may be apparent to those skilled in the art upon reading this specification, and can be made without departing from its spirit and scope. The invention is therefore to be limited only by the terms of the claims, along with the full scope of equivalents to which the claims are entitled.

Advantages of Invention

1) As a detection modality, the BPP kit protocol modality has the potential to be one of the least expensive, least invasive, and most accurate testing adjuncts available for improving available Lyme disease testing. The need for more effective technology is most assuredly present as Lyme disease is presently the fastest growing vector borne disease in this country, and a growing concern worldwide.

2) The present accepted and most effective method of testing for the actual live presence of the *Borrelia* pathogen is the class of PCR test procedures, which vary according to manufacturer. Other traditional tests only evaluate the immune response (This is a problem because the individual may have been infected previously, recovered, was treated, or had no immune response). PCR tests are now only traditionally utilized through the invasive collection of synovial fluid, cerebral spinal fluid, optic fluids, and tissue biopsy due to the higher concentrations of the Lyme *Borrelia* species in these tissues. To simplify general population testing, simple blood serum collection after the BPP protocol will enhance and expand the use of accurate PCR serum testing significantly. Also for screen testing, only blood is the acceptable source for testing according to the FDA/CDC guidelines. Utilizing the BPP previous to serum testing does not eliminate creative opportunity within this scope of Lyme Disease testing, but demands more labs create further mechanical testing options, opening up more opportunity for patent definitions of testable DNA and polymerases within the species.

3) CDC diagnostic procedures will, by necessity, require updating. The revelation of the discovery of the underreporting of this infection is making this eventuality more apparent as a result. The NIH is supporting the development of new PCR type testing, but this pre-testing BPP kit will improve the outcome of any of the PCR mediated tests, causing no patent conflicts nor NIH issues for any of the developers within this growing field of research, and improves the accuracy of all the outcomes. These technologies require inventive acceleration in development, but this fact does not apply to this specific group of claims.

4) The FDA does not approve of diagnosis based upon the testing of urine or other body fluids to define an infection from Bb. Blood serum testing is the only acceptable tissue to be used for diagnosis at this time. Blood testing also simplifies testing procedures and makes it easily available to physicians and labs, while it stays within FDA guidelines.

5) The public has lost confidence. The state legislative levels of regulation regarding the accuracy of Lyme disease testing are on the increase as well. More states are requiring Lyme test "inaccuracy disclosure statements" for patients to be provided with from the testing agents. The level of public savvy, and fear regarding this subject is escalating beyond present technology expectations, and the industry has to keep up with the demand for more. Not only are peer reviewed science periodicals recognizing the need for awareness, prevention and early detection and treatment, but it is being discussed in popular literature. For example, one study estimates a 55% testing failure rate in early stage patients. A change from an outdated mode of testing to a more accurate and reliable testing methodology to include what is already available would resolve the public demand for disease control and resolution in a timely manner.

6) As previously indicated, the BPP protocol can possibly assist in the detection of the *Babesia* co-infection through the FISH testing protocol. There are other co-infections that are involved with Lyme disease, and they are detected through laboratory testing as well. Most pathogens are not quite as difficult to test as the Bb spirochete, but this protocol has the potential to be used for the increased accuracy in the detection of *Ehrlichia* as well.

7) This protocol is not just for human testing, but also applies well to veterinary testing, as many canines, felines and equines possess the antibodies of past infections that have been treated, but they may or may not have been re-infected.

8) An unanticipated but likely conclusion is that the BPP may be used in conjunction with traditional antibiotic therapy as a pretreatment to bring the pathogen into reachable, blood filled tissues where the antibiotics can easily affect effective eradication.

The use of the *Borrelia* Provocation Procedure in conjunction with already existing testing technologies will significantly change the diagnostic accuracy, timeliness, and therefore treatment effectiveness. The potential also lies within the BPP to also improve the effectiveness of traditional treatment protocols, at any stage of the infection, due to the BPP outcome expectations.

Travel in the blood for Lyme *Borrelia* spirochetes is exceedingly slow compared to the movement in collagenous tissues in which they usually prefer to live. Unless lured into the blood, it can be virtually undetectable in blood as a pathogen, especially compared with many other bacterial infections. In addition, they actually adjust their DNA and chromosomes to adapt to the new individual's immune system, and as a result they do not readily set off the host's immune system alarms, remaining virtually invisible to the immune system. If the immunoglobulins themselves have been infected, pathogenic detection of immune response is impossible. Therefore, Bb requires a different detection method. The solution to this testing dilemma is to deliberately lure the spirochetes into the blood, within a specific time frame. This is accomplished by using the BPP protocol prior to blood testing. The testing is no longer immune system (ELISA) dependent, and therefore this makes tests for the actual detection for the presence of Bb, such as a PCR tests, quite sensitive and responsive.

Presently, PCR testing tends to be utilized in association with invasive and expensive biopsies of tissues and fluids collected from where the pathogen gathers in its greatest numbers, such as joints, heart, and nervous tissues, etc. It is generally not used for Bb detection in blood due to the low concentration of the pathogen there. Once the Lyme *Borrelia* is in the blood through the use of the BPP protocol, the PCR is the best present universally accepted choice.

By creating a controlled system of environmental variables as with the BPP, the pathogen becomes controlled, uncloaked, un-encysted, detectable, and therefore treatable in blood within a predictable time frame.

Turning now to FIGS. 1-4, views of an embodiment of a suggested injection tine device are provided. The injection tine device 20 comprises a base 12 which provides a body for the structure of the device. A balloon reservoir 16 on the base 12 is in communication with a plurality of needles 19. The needles 19 allow fluid 17 within the reservoir 16 to be ejected through them. At a bottom 11 of the device, an injection platform 18 is movable with respect to the needles 19 from a covering position that covers the needles 19, to a retracted position that exposes the needles 19. In operation, the platform 18 may be positioned against a skin of a user, and the needles 19 urged into the skin, causing the platform 18 to retract. At top plunger 13 has a spring 14 between it and the injection platform 18. The plunger 13 allows force to be applied to the device 20. As the plunger 13 is depressed against the spring 14 force, the reservoir 16 is compressed, urging fluid therein out of the needles 19. Similarly, upon the depression of the plunger 13, the needles 19 are urged out of the platform 18 and, if the platform 18 is on a soft surface such as a subject's skin, the needles will continue to pierce the skin, while the platform 18 moves to its retracted position while stabilizing the device 20. In some embodiments, the injection tine device 20 may have a safety bracket 15 that requires the plunger 13 to be twisted to break the bracket 15 and allow the plunger 13 to depress. The needles 19 may be of any size to allow the salivary gland extract to be injected into a test subject. In one embodiment, the needles are sized to mimic the injection depths of an actual tick bite. As such, the needles 19 in this embodiment may have lengths of 0.14 mm, 1 mm, 1.25 mm, 2.75 mm, 3.25 mm, and/or any combination thereof.

In a particular embodiment, small gauge (30) dermal needles of varying lengths for multiple depth injection levels in the dermis may be used. The balloon reservoir holds a saline flush to mobilize the SGE and Keratin matrix out of the inner reservoir into the needles and into the tissues. The reservoir is protected by a safety tab bracket, which is broken just prior to injection. The injection is mediated by a spring coil tension release device in the core.

The device comes to the lab in a single unit with a bottom cover of dense core foam designed to cushion the injection needles. It is untwisted, the top and bottom covers removed, and the device is ready for immediate use.

Figure 1:
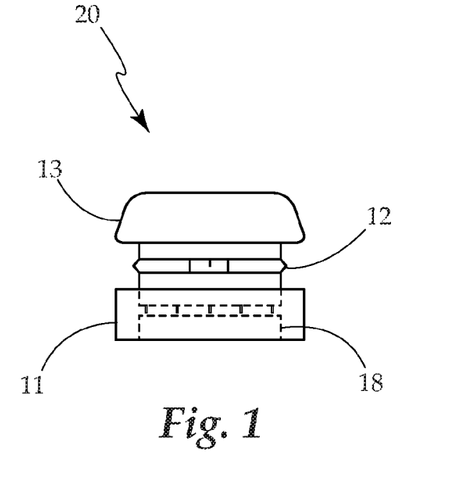
Figure 2:
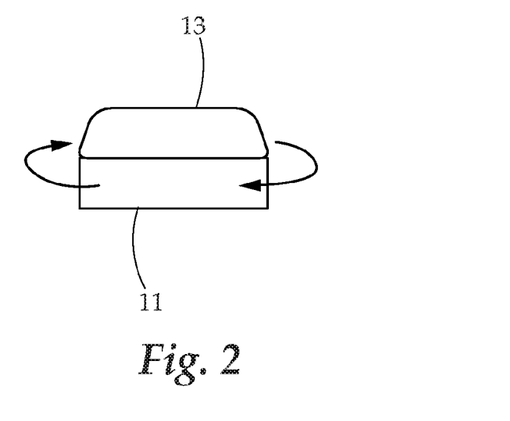
Figure 3:
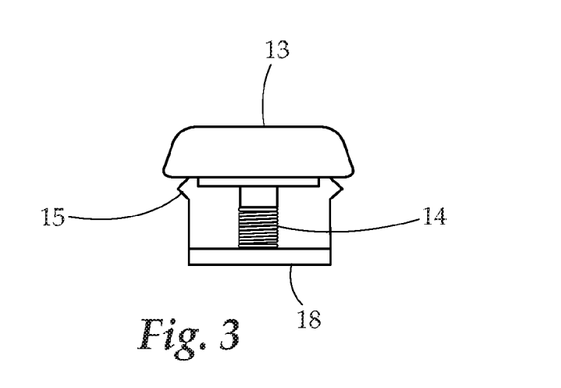
Figure 4:
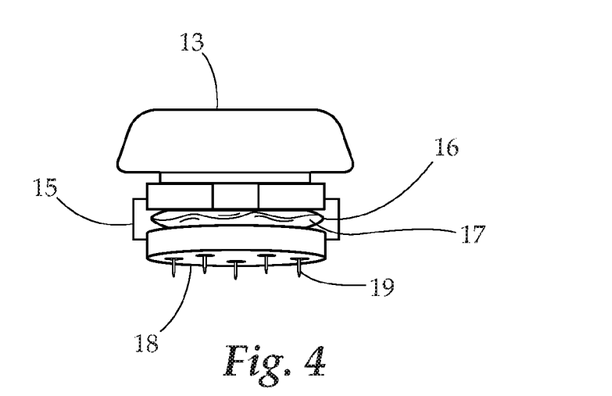
Figure 5:
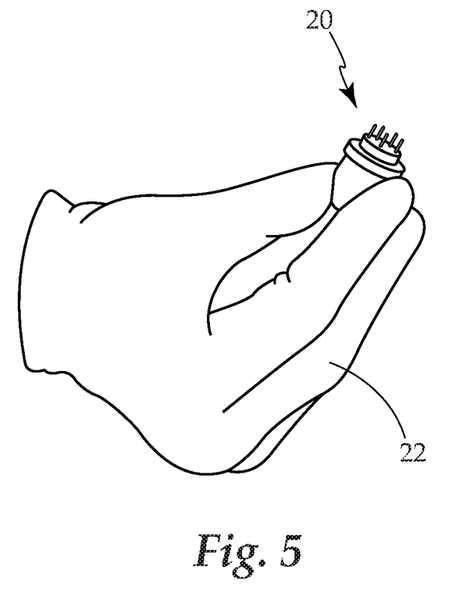
Figure 6:
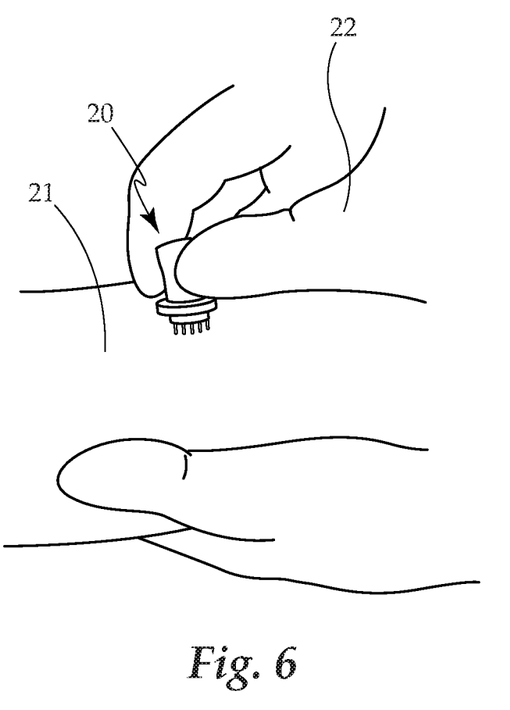

FIGS. 5 and 6 provide views of an embodiment of an injection process. The injection tine device 20 is prepared for injection of the salivary gland extract into the test subject 21 by an administrator 22. Once prepared, the device is placed on a skin of the test subject 21 and the needles inserted, allowing injection of the fluid through the needles.

In one embodiment, the placement of the BPP tine or bolus may be in the same extremity as testing will be, in order to improve testing, due to higher concentrations of spirochete numbers at the provocation site if an infection is present. The anterior of the lower arm is ideal.

In another embodiment, the administrator may place the recessed needle injection platform pad on the arm, gently but firmly, and then trigger the top plunger to release the spring for a single use, disposable injection of SGE as a *Borrelia* Provocation Procedure.

Figure 7:
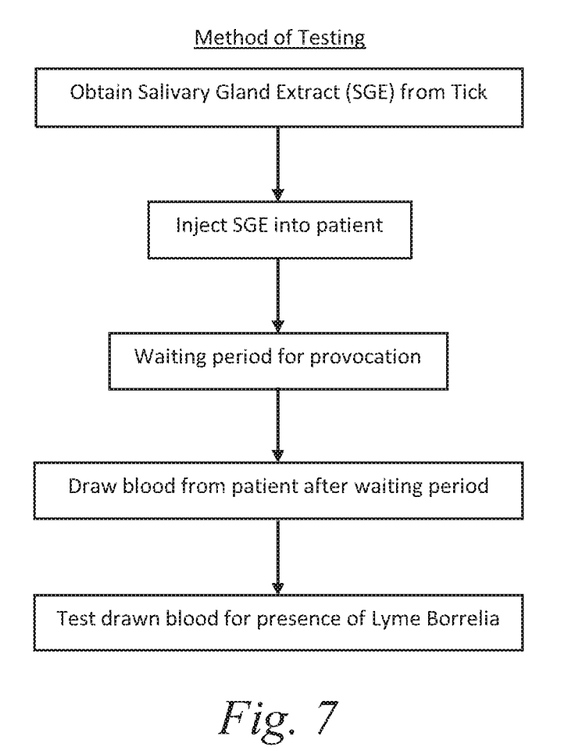

FIG. 7 provides a flow chart showing steps of an embodiment of testing. The method begins with the obtaining the salivary gland extract (SGE). The SGE may apply to either creating, purifying or otherwise extracting or generating the SGE, or may simply refer to loading a syringe or injection device with pre-prepared SGE. The obtained SGE may then be injected into a patient/test subject. This may be a human, or other mammal, depending on application. Once injected, there is a waiting period to provoke the Lyme *Borrelia* to leave its preferred tissue and enter the blood stream of the patient. After this waiting period, blood may be drawn and tested for the presence of the Lyme *Borrelia*. A presence of it indicates that an infection is present, while a lack of it indicates that there is likely no infection.

Figure 8:
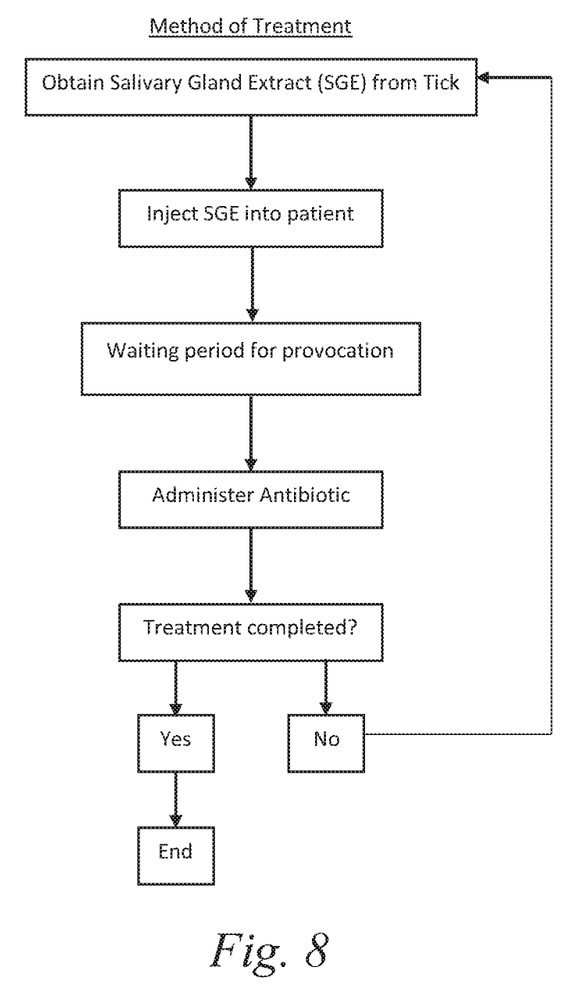
FIG. 8 provides a flow chart of an embodiment of a method of treatment for Lyme *Borrelia* infection.

FIG. 8 provides a flow chart showing steps of an embodiment of treatment. The method begins with the obtaining the salivary gland extract (SGE). The obtaining step may apply to either creating, purifying or otherwise extracting or generating the SGE, or may simply refer to loading a syringe or injection device with pre-prepared SGE. The obtained SGE may then be injected into a patient/test subject. This may be a human, or other mammal, depending on application. Once injected, there is a waiting period to provoke the Lyme *Borrelia* to leave its preferred tissue and enter the blood stream of the patient. Once the Lyme *Borrelia* is exposed in the blood after this waiting period, it is susceptible to treatment by traditional antibiotics which also are carried through the body through blood. In some embodiments, treatment may be repeated to ensure complete eradication of the Lyme *Borrelia*.

BPP may be applied to routine blood testing for Lyme disease and is unique as it has not been performed on humans, nor used as a diagnostic platform in and of itself. Blood is the easiest to access tissue for testing. There is no harm as tick saliva activity is short lived and even if artificially produced, it will still dissipate naturally in an uninfected individual. Within an infected person, it cannot aggravate the condition as they already carry the agent of infection.

Despite utilization of portions of several prior arts: 1) saliva injection, 2) production of saliva or extraction of saliva, 3) production of keratin-like substances, and the use of 4) PCR testing, and the unique combination of this entire procedure combined has not been utilized for defining an active Lyme disease infection or treating Lyme disease in humans.

The utilization of this kind of protocol for the treatment of human and animal active Lyme disease infection is completely without prior art. The methodology opening to this possibility of treatment was inferred by prior immunological studies. The studies state, in essence, that 4-6 days after injection of tick saliva into mice, the spirochete concentration in dense tissues (heart) decreased and in dermal surface tissues the concentration increased. This patent postulates that manipulating this natural reaction creates antibiotic bioavailability of the spirochete pathogens within humans. The issues of possible diagnosis and treatment has never been discussed in these researches, only the immune responses and modulations from this team's studies.

Prior Arts Concepts Referenced and Unified Novel Applications

Tick saliva extracts have been studied and are a standard substance of procurement for research facilities for almost two decades, and is only a tool in this *Borrelia* Provocation Procedure protocol. There are many avenues of natural and there is always synthetic manufacture as a future development.

The production and use of keratin-like substances are also a standard in laboratory procedures. There are many variants, and only one specific form has been discussed in this document.

The chemotaxic migration and observed manipulation of the *Borrelia* spirochete was a research topic of Chen-Ming Shih and others at the Department of Parasitology and Tropical Medicine in Taipei, China. The focus of this institute and its researchers is simply the defining and identification of a relatively new invasion of the disease to Taiwan. The behavior of the spirochete is the focus of their studies, and no mention of human testing, treatment nor are vaccines discussed here. The primary weakness of their research, which had to be compensated for within the scope of this patent, is that their research is in vitro, which substantially alters normal behavior of these sensitive spirochetes. The key of their research which applies to this patent is that the association of the saliva factors mediates transmission of the *Borrelia* spirochete, but the mechanism responsible is not yet defined. As a result the use of bio-identical tick saliva is required in its entirety to mediate the provocation response the BPP triggers. It is a key point here, but not the focus of these researchers or this institution.

The use of a PCR technology is almost expected a technology in modern science, particularly concerning detection and immunology today. It is now the standard tool of the diagnostic and manufacturing medical and chemical science industries. Its use for this patent does not alter this patent, nor is the patent dependent upon it. It is the best of the detection tools to apply after the BPP is utilized.

This combination of the prior arts is not obvious, as each factor of research is targeting their specific subjects in different unrelated areas of science arts—behavioral entomology and human immunology. The combinations presented in this patent cannot be inferred through the present directional paths of each of the research avenues and studies or the individuals or organizations behind them. There seems to be no direct route to the conclusions of testing and treatment for humans from the sources of the parts of this co-related information, as presented for the *Borrelia* Provocation Procedure.

In summary, and as can be seen from the prior discussion, there is a potential for the use of the PCR, or polymerase chain reaction, testing using the spirochete DNA itself, but because of traditionally low numbers of spirochetes in the blood, this test has not been reliable.

The least invasive and most economical manner of Lyme testing is using blood. Existing PCR testing had been proven to be quite effective in identifying Bb and all other strains of Lyme *Borrelia*, previously from specimens obtained from other deep tissues that have been biopsied (an invasive and expensive procedure), but not blood due to low concentrations. Utilizing the Lyme *Borrelia* provocation procedures discussed herein, with PCR detection methods, as an effective and accurate testing method can be simply utilized with blood as the source. The same is true for traditional testing of co-infective agents.

Lyme *Borrelia* live in the central nervous system, joints, and connective tissue. They do not typically live in the blood stream, at least not in significant amounts, so it can easily be missed when examining and testing blood. So if a lab finds them in the blood without a BPP in small amounts it generally is an indicator that there is a high amount in other tissues in the body. With the co-infections, the detection rates are also sporadic and difficult to detect without specific testing indicated from symptoms. The BPP testing protocol may increase the concentrations of the co-infection into the blood by its own co-infective nature of re-infection, possibly improving their rates of detection as well.

With the utilization of the BPP, the artificial stimulation of the natural reaction of the pathogen is to release the spirochetes into the blood from avascular tissues, therefore facilitating accurate, specific, and sensitive testing, creating a new gold standard for Lyme detection. If the *Borrelia* and co-infective pathogens are manipulated in a controlled fashion into the blood stream, they are easily detected with extreme accuracy in an extraordinarily non-invasive and safe fashion, solving most of the Lyme Disease Laboratory Testing problems and utilizing presently available technologies to accomplish this.

While several variations of the present invention have been illustrated by way of example in preferred or particular embodiments, it is apparent that further embodiments could be developed within the spirit and scope of the present invention, or the inventive concept thereof. However, it is to be expressly understood that such modifications and adaptations are within the spirit and scope of the present invention, and are inclusive, but not limited to the following appended claims as set forth.

What is claimed is:

1. A method of testing for a presence of a Lyme *Borrelia* infection comprising the steps of:
   injecting a salivary gland extract of a tick into a test subject;
   waiting for a period of approximately 24 hours to five days to allow the injected salivary gland extract to provoke the Lyme *Borrelia* to enter a blood stream of the test subject;
   drawing a quantity of blood from the test subject after the waiting period;
   testing the drawn quantity of blood for a presence of the Lyme *Borrelia*, the testing determining if Lyme *Borrelia* infection is present.

2. The method of testing of claim 1 wherein the step of injecting is performed using an injection tine device comprising a plurality of needles.

3. The method of testing of claim 2 wherein the injection tine device used in the injection step comprises the plurality of needles having at least two of the lengths of 0.14 mm; 1 mm; 1.25 mm; 2.75 mm and 3.75 mm, the needle length selected to mimic an introduction of the salivary gland extract by a living tick.

4. The method of testing of claim 1 wherein the salivary gland extract comprises a keratin matrix based carrier, configured to slow a dispersion of the salivary gland extract once injected.

5. The method of testing of claim 1 wherein the step of injecting the salivary gland extract comprises injecting the salivary gland extract into an area of the test subject, and wherein the step of drawing the quantity of blood comprises drawing the quantity of blood from within approximately six inches from the injection area.

6. The method of testing of claim 1 wherein the step of testing comprises performing a polymerase chain reaction test on the drawn blood; and
   detecting Lyme *Borrelia* DNA based on the performed polymerase chain reaction.

7. The method of testing of claim 1 further comprising the step of testing the drawn blood for co-infections, the co-infections being at least one of: *Babesia, Erlichia, Bartonella*, tick born encephalitis, and Rocky Mountain Spotted Fever.

8. A method of treatment of a Lyme *Borrelia* infection comprising the steps of:
   injecting a salivary gland extract of a tick into a test subject; and
   applying a treatment protocol after a period of approximately 24 hours or greater after the injecting step to allow the injected salivary gland extract to provoke the Lyme *Borrelia* in the test subject to enter a blood stream of the test subject.

9. The method of treatment of claim 8 wherein the step of injecting is performed using an injection tine device comprising a plurality of needles.

10. The method of treatment of claim 9 wherein the injection tine device used in the injection step comprises the plurality of needles having at least two of the lengths of 0.14 mm; 1 mm; 1.25 mm; 2.75 mm and 3.75 mm, the needle length selected to mimic an introduction of the salivary gland extract by a living tick.

11. The method of treatment of claim 8 wherein the step of applying the treatment protocol comprises administering an antibiotic to the test subject.

12. The method of treatment of claim 8 further comprising the steps of drawing a quantity of blood from the test subject after the applying the treatment protocol; and
   testing the drawn quantity of blood for a presence of the Lyme *Borrelia*, the testing determining if Lyme *Borrelia* infection is present.

13. A method of testing for a presence of a Lyme *Borrelia* infection comprising the steps of:
   injecting a salivary gland extract of a tick into a test subject;
   waiting for a period of approximately 24 hours to five days;
   drawing a quantity of blood from the test subject after the waiting period;
   testing the drawn quantity of blood for a presence of the Lyme *Borrelia*.

14. The method of testing of claim 13 wherein the step of injecting the salivary gland extract comprises injecting the salivary gland extract into an area of the test subject, and wherein the step of drawing the quantity of blood comprises drawing the quantity of blood from within approximately six inches from the injection area.

15. The method of testing of claim 13 wherein the step of testing comprises performing a polymerase chain reaction test on the drawn blood; and
   detecting Lyme *Borrelia* DNA based on the performed polymerase chain reaction.

16. The method of testing of claim 13 further comprising the step of testing the drawn blood for co-infections, the co-infections being at least one of: *Babesia, Erlichia, Bartonella*, tick born encephalitis, and Rocky Mountain Spotted Fever.

* * * * *